(12) United States Patent
Ahn et al.

(10) Patent No.: US 8,916,602 B2
(45) Date of Patent: Dec. 23, 2014

(54) FUSARISETIN COMPOUNDS, AND USE THEREOF

(75) Inventors: Jong Seog Ahn, Daejeon (KR);
Jae-Hyuk Jang, Daejeon (KR); Bo Yeon Kim, Daejeon (KR); JunPhil Jang, Daejeon (KR); Yukihiro Asami, Daejeon (KR); Hyuncheol Oh, Busan (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 13/811,133

(22) PCT Filed: Jul. 20, 2011

(86) PCT No.: PCT/KR2011/005348
§ 371 (c)(1),
(2), (4) Date: Jan. 18, 2013

(87) PCT Pub. No.: WO2012/011741
PCT Pub. Date: Jan. 26, 2012

(65) Prior Publication Data
US 2013/0116297 A1    May 9, 2013

(30) Foreign Application Priority Data

Jul. 20, 2010    (KR) .......................... 10-2010-0070131
Jul. 20, 2011    (KR) .......................... 10-2011-0072017

(51) Int. Cl.
| | |
|---|---|
| *A61K 31/407* | (2006.01) |
| *C07D 491/048* | (2006.01) |
| *C07D 491/04* | (2006.01) |
| *A23L 1/30* | (2006.01) |
| *A23L 1/28* | (2006.01) |

(52) U.S. Cl.
CPC .......... *C07D 491/048* (2013.01); *C07D 491/04* (2013.01); *A23L 1/3002* (2013.01); *A23L 1/28* (2013.01); *A23V 2002/00* (2013.01)
USPC ........................................ 514/410; 548/418

(58) Field of Classification Search
CPC ................................................... C07D 491/048
USPC .......................................................... 548/418
See application file for complete search history.

(56) References Cited

PUBLICATIONS

Jang, et al. Document No. 154:534449, retrieved from STN, Apr. 20, 2011.*
Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
Jang, et al. J. Am. Chem. Soc. 2011, 133, 6865-6867.*
Bezuidenhout, S.C., et al., Structure Elucidation of the Fumonisins . . . , J. Chem., Soc. Chem., Commun., pp. 743-745, 1988.
Burke, L.T., et al., A Short Stereoselective Total Synthesis of the Fusarium . . . , Organic Letters, vol. 2, No. 23, pp. 3611-3613, 2000.
Gelderblom, W.C., et al., Fumonisins—Novel Mycotoxins With Cancer-Promoting . . . , Applied & Environmental Microbiology, vol. 54, No. 7, pp. 1806-1811, 1988.
Pereira, C., et al., Total Synthesis of the Sphingolipid Biosynthesis . . . , J. Am. Chem. Soc., vol. 131, pp. 6066-6067, 2009.

* cited by examiner

*Primary Examiner* — Shawquia Jackson
(74) *Attorney, Agent, or Firm* — Lucas & Mercanti, LLP

(57) ABSTRACT

The present invention relates to novel fusarisetin compounds separated from *Fusarium* sp. FN080326 and having an anticancer activity, and to the use thereof. In detail, novel fusarisetin compounds separated and purified from *Fusarium* sp. FN080326, which is in turn separated from a soil sample, have an inhibitory activity on the proliferation and transfer of cancer cells such as breast cancer cells, liver cancer cells or myeloid leukemic cells. Therefore, the compounds can be effectively used for anticancer compositions containing the compounds as active ingredients.

7 Claims, 9 Drawing Sheets

SEQUENCE LISTING

```
<160> NUMBER OF SEQ ID NOS: 3

<210> SEQ ID NO 1
<211> LENGTH: 506
<212> TYPE: DNA
<213> ORGANISM: Fusarium oxysporum

<400> SEQUENCE: 1
agggatcatt accgagttta caactcccaa acccctgtga acatacctat acgttgcctc     60
ggcggatcag cccgcgcccc gtaaaacggg acggcccgcc cgaggaccct aaactctgtt    120
tttagtggaa cttctgagta aaacaaacaa ataaatcaaa actttcaaca acggatctct    180
tggttctggc atcgatgaag aacgcagcaa aatgcgataa gtaatgtgaa ttgcagaatt    240
cagtgaatca tcgaatcttt gaacgcacat tgcgcccgcc agtattctgg cgggcatgcc    300
tgttcgagcg tcatttcaac cctcaagctc agcttggtgt tgggactcgc ggtaacccgc    360
gttccccaaa tcgattggcg gtcacgtcga gcttccatag cgtagtaata atacacctcg    420
ttactggtaa tcgtcgcggc cacgccgtaa aaccccaact tctgaatgtt gacctcggat    480
caggtaggaa tacccgctga acttaa                                         506
```

<210> SEQ ID NO 2
<211> LENGTH: 563
<212> TYPE: DNA
<213> ORGANISM: Fusarium oxysporum

<400> SEQUENCE: 2

| | | | | | |
|---|---|---|---|---|---|
| aaaccaacag | ggattgccct | agtaacggcg | agtgaagcgg | caacagctca | aatttgaaat | 60 |
| ctggctctcg | ggcccgagtt | gtaatttgta | gaggatgctt | ttgatgcggt | gccttccgag | 120 |
| ttccctggaa | cgggacgcca | tagagggtga | gagcccgtc | tggttggata | ccaaatctct | 180 |
| gtaaagctcc | ttcgacgagt | cgagtagttt | gggaatgctg | ctctaaatgg | gaggtatatg | 240 |
| tcttctaaag | ctaaatactg | gccagagacc | gatagcgcac | aagtagagtg | atcgaaagat | 300 |
| gaaaagcact | ttgaaaagag | agttaaaaag | tacgtgaaat | tgttgaaagg | gaagcgttta | 360 |
| tgaccagact | tgggcttgga | taatcatctg | gggttctccc | cagtgcactt | ttccagtcca | 420 |
| ggccagcatc | agttttcgcc | gggggataaa | ggcttcggga | atgtggctcc | ctccggggag | 480 |
| tgttatagcc | cgttgcgtaa | taccctggcg | gggactgagg | ttcgcgcatc | tgcaaggatg | 540 |
| ctggcgtaat | ggtcatcaac | gac | | | | 563 |

<210> SEQ ID NO 3
<211> LENGTH: 1675
<212> TYPE: DNA
<213> ORGANISM: Fusarium oxysporum

<400> SEQUENCE: 3

| | | | | | |
|---|---|---|---|---|---|
| cattataccg | cgaaactgcg | aatggctcat | tatataagtt | atcgtttatt | tgatagtacc | 60 |
| ttactacttg | gataaccgtg | gtaattctag | agctaataca | tgctaaaaat | cccgacttcg | 120 |
| gaagggatgt | atttattaga | ttaaaaacca | atgcccttcg | gggctcactg | gtgattcatg | 180 |
| ataactcctc | gaatcgcatg | gccttgtgcc | ggcgatggtt | cattcaaatt | tcttccctat | 240 |
| caactttcga | tgtttgggta | ttggccaaac | atggttgcaa | cgggtaacgg | agggttaggg | 300 |
| ctcgaccccg | gagaaggagc | ctgagaaacg | gctactacat | ccaaggaagg | cagcaggcgc | 360 |
| gcaaattacc | caatcccgac | acggggaggt | agtgacaata | aatactgata | cagggctctt | 420 |
| ttgggtcttg | taattggaat | gagtacaatt | taaatccctt | aacgaggaac | aattggaggg | 480 |
| caagtctggt | gccagcagcc | gcggtaattc | cagctccaat | agcgtatatt | aaagttgttg | 540 |
| tggttaaaaa | gctcgtagtt | gaaccttggg | cctggccgtc | cggtccgcct | caccgcgtgt | 600 |
| actggctcgg | ccgggccttt | ccctctgtgg | aaccccatgc | ccttcactgg | gcgtggcggg | 660 |
| gaaacaggac | ttttactgtg | aaaaaattag | agtgctccag | gcaggcctat | gctcgaatac | 720 |
| attagcatgg | aataatagaa | taggacgtgt | ggttctattt | tgttggtttc | taggaccgcc | 780 |
| gtaatgatta | atagggacag | tcgggggcat | cagtattcaa | ttgtcagagg | tgaaattctt | 840 |
| ggatttattg | aagactaact | actgcgaaag | catttgccaa | ggatgttttc | attaatcagg | 900 |
| aacgaaagtt | aggggatcga | agacgatcag | ataccgtcgt | agtcttaacc | ataaactatg | 960 |
| ccgactaggg | atcggacggt | gttatttttt | gacccgttcg | gcaccttacg | agaaatcaaa | 1020 |
| gtgcttgggc | tccaggggga | gtatggtcgc | aaggctgaaa | cttaaagaaa | ttgacggaag | 1080 |
| ggcaccacca | ggggtggagc | ctgcggctta | atttgactca | acacggggaa | actcaccagg | 1140 |
| tccagacaca | atgaggattg | acagattgag | agctctttct | tgattttgtg | ggtggtggtg | 1200 |
| catggccgtt | cttagttggt | ggagtgattt | gtctgcttaa | ttgcgataac | gaacgagacc | 1260 |

-continued

```
ttaacctgct aaatagcccg tattgctttg gcagtacgct ggcttcttag agggactatc    1320
ggctcaagcc gatggaagtt tgaggcaata acaggtctgt gatgccctta gatgttctgg    1380
gccgcacgcg cgctacactg acggagccag cgagtacttc cttgtccgaa aggtccgggt    1440
aatcttgtta aactccgtcg tgctggggat agagcattgc aattattgct cttcaacgag    1500
gaatccctag taagcgcaag tcatcagctt gcgttgatta cgtccctgcc ctttgtacac    1560
accgcccgtc gctactaccg attgaatggc tcagtgaggc gtccggactg gcccagagag    1620
gtgggcaact accactcagg gccggaaagc tctccaaact cggtcattag agaag         1675
```

FUSARISETIN COMPOUNDS, AND USE THEREOF

CROSS-REFERENCE TO RELATED APPLICATIONS

This application is a 371 of PCT/KR2011/005348, filed on Jul. 20, 2011, which claims the benefit of Korean Patent Application Nos. 10-2010-0070131 filed Jul. 20, 2010 and 10-2011-0072017 filed on Jul. 20, 2011, the contents of which are incorporated herein by reference.

BACKGROUND OF THE INVENTION

1. Field of the Invention

The present invention relates to a fungus having an anticancer activity which is separated from a soil sample, to compounds having an inhibitory activity on the proliferation and metastasis of cancer cells which are produced from the said fungus, to anticancer compositions comprising the said compounds as active ingredients, and methods for the separation of the said compounds.

2. Description of the Related Art

Cancer is a critical disease that is recording $1^{st}$ mortality in modern society. Even after all the treatment methods developed so far, a revolutionary treatment method for cancer is still in request. In the field of modern medicine, cancer treatment method is exemplified by surgical operation, biotherapy, radiotherapy, and chemotherapy using anticancer agents. Chemotherapy is to treat metastatic cancer by suppressing cancer cell proliferation by administering anticancer agents via oral administration or injection, which has been used as a standard therapy for the treatment of metastatic cancer. Chemotherapy cannot treat metastatic cancer completely, but still plays an important role in extending patient's life with relieving cancer symptoms.

Among the many anticancer agents developed from natural products, taxol has been most widely used for the treatment of breast cancer and ovarian cancer. Those chemotherapeutic agents have problems of side effects and cancer chemoresistance in the increase. Despite studies on cancer have been actively going on, the development of a novel anticancer agent with less side effects and overcoming resistance problem is still difficult because of diversity and different development mechanisms of cancer.

Study on the screening and use of natural substance is focused on investigating biosynthesis capability of organisms, which has been targeting largely plants and microorganisms up to date. In particular, microorganisms have been fascinating targets for searching physiological active substances because of diversity in species, capability of producing interesting physiological active substances, short generation time, availability for mass production, and industrial usability. Many physiological active substances screened from microorganisms are separated from *Actinomycetes*, fungi, and bacteria. 25% out of total physiological active substances separated from microorganisms are originated from fungi, suggesting that fungi are industrially or medically important microorganisms producing physiological active substances including anticancer materials.

Thus, the present inventors searched a substance having an excellent anticancer activity from metabolites of soil microorganisms. In the midst, the inventors separated a fungus strain *Fusarium* sp. FN080326 producing an anticancer material having an excellent anticancer activity from a soil sample, from which the inventors separated and purified novel fusarisetin compounds. The present inventors completed this invention at last by confirming that the said fusarisetin compounds had an inhibitory activity on the proliferation and metastasis of cancer cells such as breast cancer cells, liver cancer cells or myeloid-leukemic cells.

SUMMARY OF THE INVENTION

It is an object of the present invention to provide a fungus strain (*Fusarium* sp. FN080326) having an anticancer activity which is separated from a soil sample and novel fusarisetin compounds having an inhibitory activity on the proliferation and metastasis of cancer cells produced by the said fungus.

It is another object of the present invention to provide a method for producing the fusarisetin compounds of the present invention.

It is also an object of the present invention to provide a novel strain producing the fusarisetin compounds of the present invention.

It is further an object of the present invention to provide an anticancer composition comprising the fusarisetin compounds of the present invention.

It is also an object of the present invention to provide a method for the prevention or treatment of cancer using the fusarisetin compounds of the present invention.

To achieve the above objects, the present invention provides the compound represented by [formula 3] or pharmaceutically acceptable salts thereof:

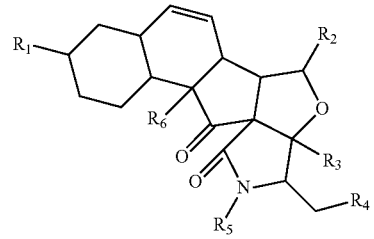

[Formula 3]

Wherein, R1, R2, R3, R4, R5, and R6 are independently H, methyl, ethyl, propyl, isopropyl, butyl, isobutyl, acetyl, benzyl, halogen atom, OH, or carboxyl group, and contain isomers at all asymmetric carbons.

The present invention also provides a pharmaceutical composition for the prevention and treatment of cancer comprising the said compound as an active ingredient.

The present invention also provides a health food for the prevention and improvement of cancer comprising the said compound as an active ingredient.

The present invention also provides a method for producing the said compound.

The present invention also provides a fungus strain *Fusarium* sp. FN080326 producing the said compound which has been deposited under the Accession No. of KCTC11985BP.

The present invention also provides a treatment method for cancer containing the step of administering a pharmaceutically effective dose of the said compound or pharmaceutically acceptable salts thereof to a subject having cancer.

The present invention also provides a prevention method for cancer containing the step of administering a pharmaceutically effective dose of the said compound or pharmaceutically acceptable salts thereof to a subject.

The present invention also provides the said compound or pharmaceutically acceptable salts thereof for the use as a pharmaceutical composition for the prevention and treatment of cancer.

The present invention also provides the said compound or pharmaceutically acceptable salts thereof for the use as a health food for the prevention and improvement of cancer.

Advantageous Effect

As explained hereinbefore, the novel fusarisetin compound of the present invention has an excellent inhibitory effect on the proliferation and metastasis of various cancer cells, so that the fusarisetin compound can be effectively used as an anticancer agent.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
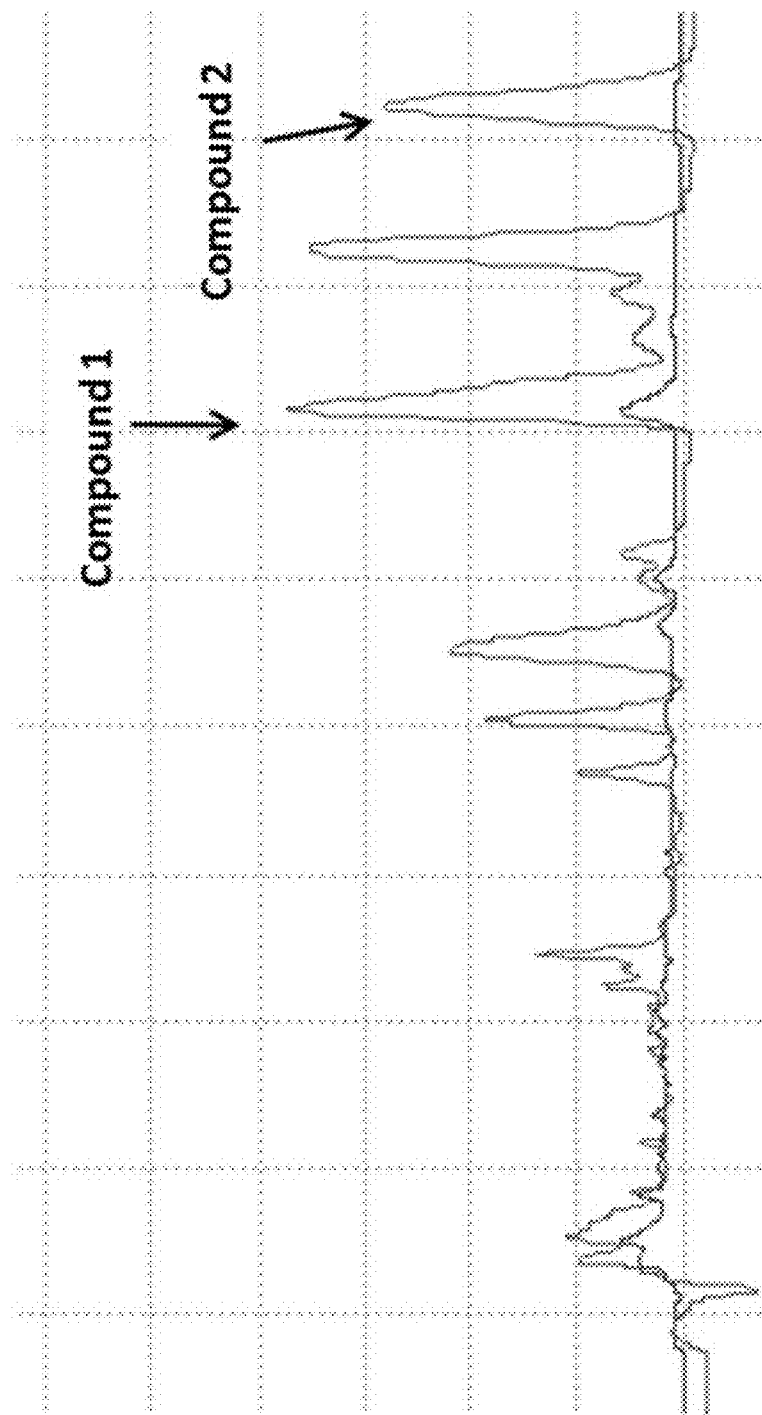
FIG. 1 is a diagram illustrating HPLC chromatogram of the compound 1 and compound 2 (fusarisetin A and B) separated in this invention.
Figure 2:
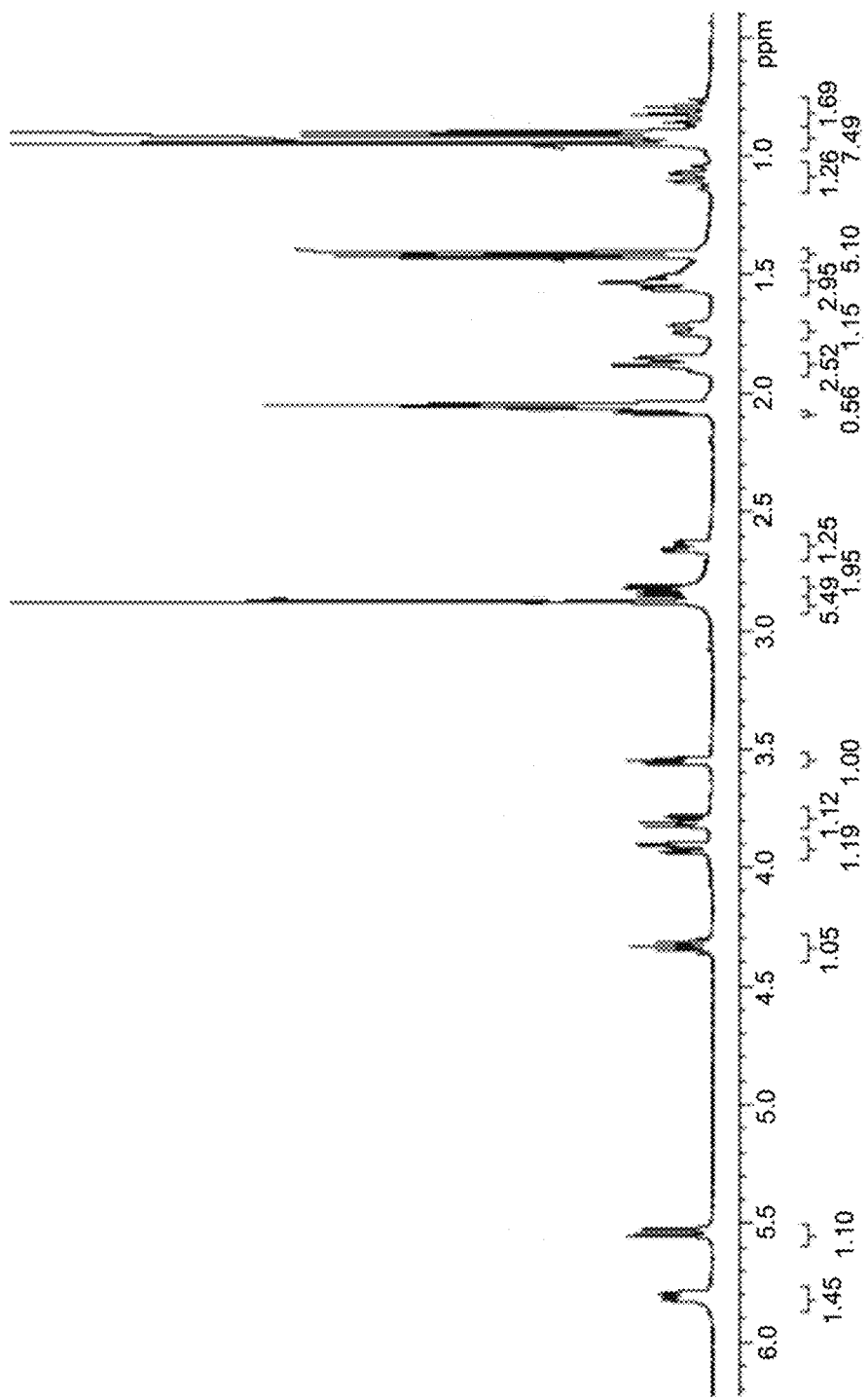
FIG. 2 is a diagram illustrating $^1$H NMR spectrum (400 MHz, Acetone-$d_6$) of the compound 1 (fusarisetin A) separated in this invention.
Figure 3:
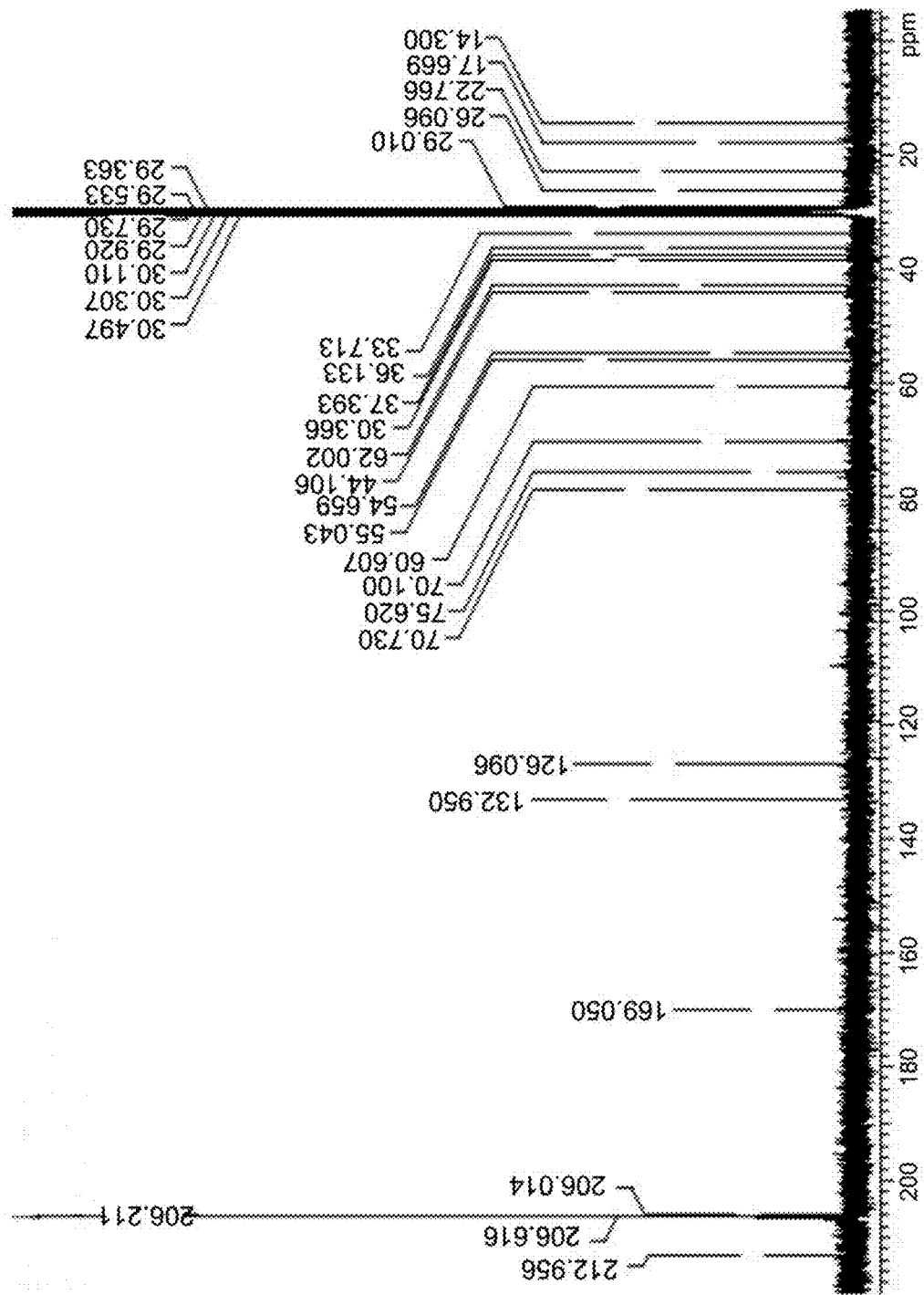
FIG. 3 is a diagram illustrating $^{13}$C NMR spectrum (100 MHz, Acetone-$d_6$) of the compound 1 (fusarisetin A) separated in this invention.
Figure 4:
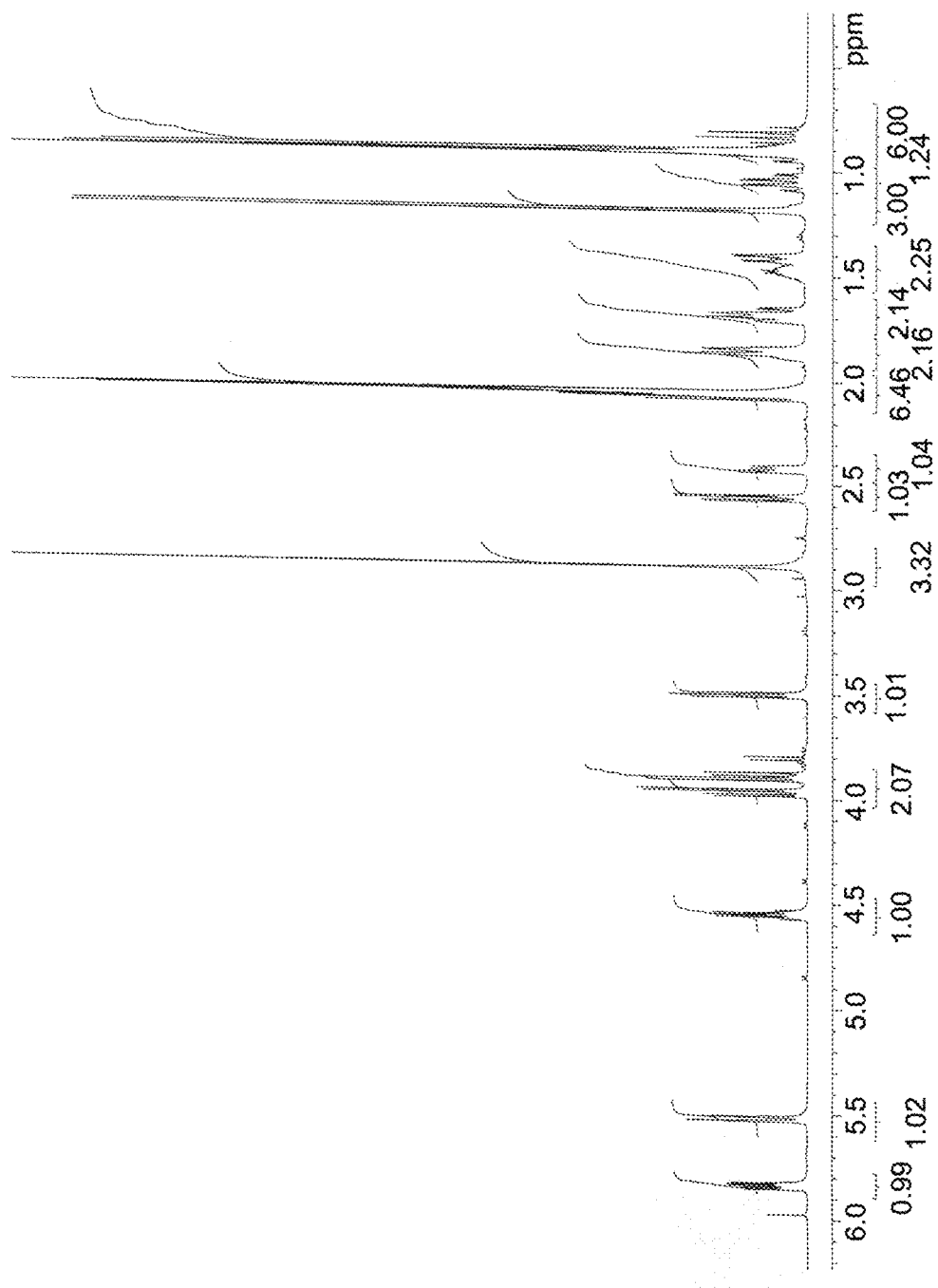
FIG. 4 is a diagram illustrating $^1$H spectrum (400 MHz, Acetone-$d_6$) of the compound 2 (fusarisetin B) separated in this invention.
Figure 5:
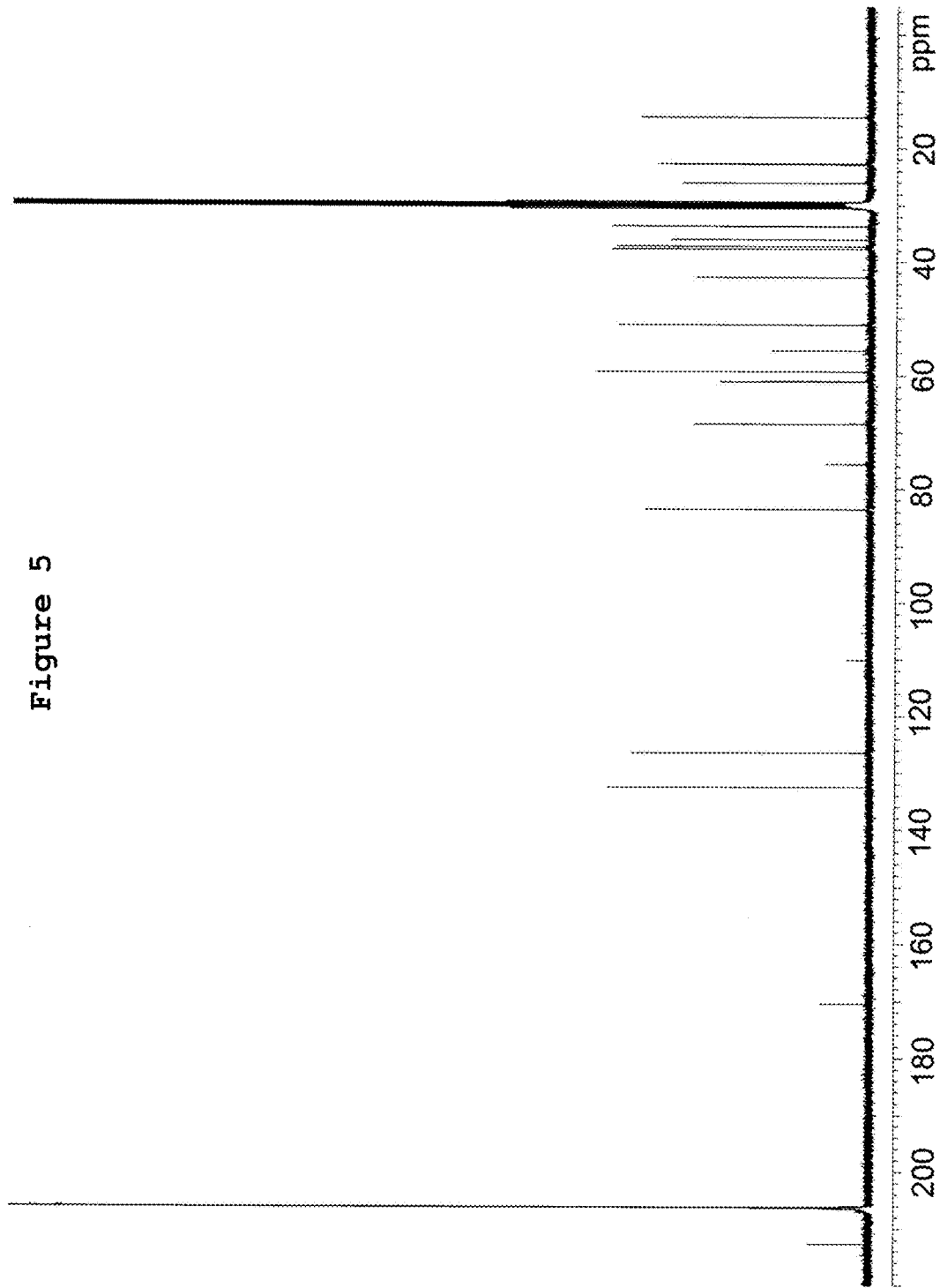
FIG. 5 is a diagram illustrating $^{13}$C NMR spectrum (100 MHz, Acetone-$d_6$) of the compound 2 (fusarisetin B) separated in this invention.

Hereinafter, the present invention is described in detail.
The present invention provides the compound represented by [formula 3] or pharmaceutically acceptable salts thereof:

[Formula 3]

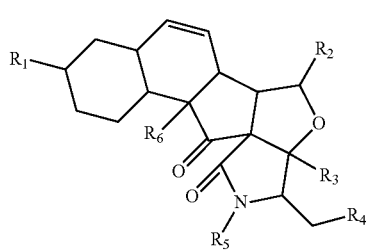

Wherein, R1, R2, R3, R4, R5, and R6 are independently H, methyl, ethyl, propyl, isopropyl, butyl, isobutyl, acetyl, benzyl, halogen atom, OH, or carboxyl group, and contain isomers at all asymmetric carbons.

The compound represented by [formula 3] is preferably the fusarisetin A compound represented by [formula 1], but not always limited thereto:

[Formula 1]

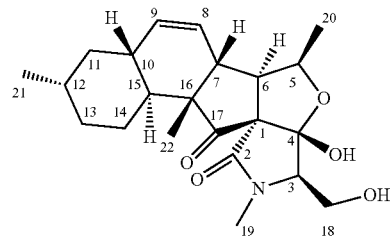

The compound represented by [formula 3] is preferably the fusarisetin B compound represented by [formula 2], but not always limited thereto:

[Formula 2]

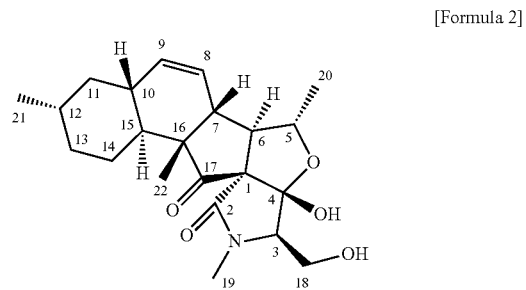 [SMILES: C[C@H]1CC[C@H]2[C@@H](C=C[C@@H]3[C@H]4[C@H](C)O[C@]5(O)[C@@H](CO)N(C)C(=O)[C@]45C(=O)[C@@]32C)C1]

The fusarisetin compound herein is preferably separated from a fungus strain *Fusarium* sp. FN080326, but not always limited thereto.

The fusarisetin compound herein has an inhibitory activity on the proliferation and metastasis of cancer cells such as breast cancer cells, liver cancer cells or myeloid leukemic cells, but not always limited thereto.

The cancer herein is preferably breast cancer, liver cancer, or myeloid leukemia, and more preferably breast cancer, but not always limited thereto.

The present invention includes not only the fusarisetin compound represented by [formula 3] or pharmaceutically acceptable salts thereof, but also solvates and hydrates possibly produced from the same.

The fusarisetin compound represented by [formula 3] of the present invention can be used in the form of a pharmaceutically acceptable salt. As for the pharmaceutically acceptable salt, it is preferably an acid addition salt prepared by using a pharmaceutically acceptable free acid. The acid addition salt can be obtained from inorganic acids such as hydrochloric acid, nitric acid, phosphoric acid, sulfuric acid, hydrobromic acid, hydroiodic acid, nitrous acid, and phosphorous acid, or non-toxic organic acids such as aliphatic mono- and dicarboxylate, phenyl-substituted alkanoate, hydroxyalkanoate and alkandioate, aromatic acids, and aliphatic and aromatic sulfonic acids. Such pharmaceutically acceptable salt includes sulfate, pyrosulfate, bisulfate, sulfite, bisulfate, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutylate, caprate, heptanoate, propiolate, oxalate, malonate, succinate, suberate, sebacate, fumarate, malate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, β-hydroxybutylate, glycolate, malate, tartrate, methanesulfonate, propanesulfonate, naphthalene-1-sulfonate, naphthalene-2-sulfonate, or mandelate.

The acid addition salt of the present invention can be obtained by the conventional method. For example, the acid addition salt can be prepared by dissolving the fusarisetin compound represented by [formula 3] in excessive acid solution, and precipitating the salt in water-miscible organic solvent such as methanol, ethanol, acetone, or acetonitrile.

The acid addition salt can be also prepared by heating the equal amount of the fusarisetin compound represented by [formula 1] and acid or alcohol in water, and evaporating the mixture, or by suction-filtering the precipitated salt.

It is also possible to produce a pharmaceutically acceptable metal salt using base. Alkaline metal or alkaline earth metal salt can be prepared by the following steps: the compound is dissolved in excessive alkaline metal hydroxide or alkaline earth metal hydroxide solution; the non-dissolved compound salt is filtered; and the remaining solution is evaporated and dried. At this time, the prepared metal salt is preferably sodium, potassium, or calcium salt. Likewise, silver salt can be obtained by reacting the alkaline metal or alkaline earth metal salt with a proper silver salt (for example, silver nitrate).

In this invention, a fungus strain was isolated from a soil sample, followed by sequencing the strain. Then, GenBank search was carried out with the obtained sequence. As a result, the strain demonstrated 99% homology with *Fusarium oxysporum* (DQ916150) and 99% homology with *Fusarium incarnatum* (EU111657). Therefore, the present inventors identified the strain as *Fusarium* sp. and then named it *Fusarium* sp. FN080362, which was deposited at Korean Collection for Type Culture (KCTC), Korea Research Institute of Bioscience and Biotechnology (KRIBB) on Jul. 18, 2011 (Accession No: KCTC11985BP).

In this invention, the culture solution of *Fusarium* sp. FN080326 was extracted with the equal volume of ethylacetate and then the extract was concentrated by vacuum evaporation. An active fraction was obtained from the concentrate by using column chromatography, followed by concentration under the reduced pressure. Using high performance liquid chromatography (HPLC), the compounds 1 and 2 of the present invention were isolated (see FIG. 1).

In this invention, the molecular weights and molecular formulas of the compounds 1 and 2 isolated from the culture solution of *Fusarium* sp. FN080326 were determined by using Electrospray Ionization mass spectrometer. Nuclear magnetic resonance (NMR) was also performed to give $^1$H NMR, $^{13}$C NMR, COSY (Correlation Spectroscopy), HMQC (1H-Detected heteronuclear Multiple-Quantum Coherence), HMBC (Heteronuclear Multiple-Bond Coherence), DEPT (Distortionless Enhancement by Polarization), and NOESY (Nuclear Overhauser effect spectroscopy) spectrums. By which, the molecular structures of the compounds 1 and 2 were identified. As a result, The compound 1 and compound 2 were identified as the compounds with novel structure in which 6-6-5-5-5 ring chains were connected one another as shown in the following formula (FIGS. 2, 3, 4, and 5). Thus, the compound 1 and compound 2 were named as fusarisetin A and fusarisetin B. HRESIMS and NMR were performed with the fusarisetin A and fusarisetin B. As a result, it was confirmed that their molecular weights were 389 each and molecular formula was $C_{22}H_{31}NO_5$. From the results of $^1$H NMR and NOESY, it was also confirmed that the compounds 1 and 2 were the isomers having the same molecular weight and molecular formula with different three-dimensional coordinations of $C_5$.

In this invention, to investigate whether or not the fusarisetin A and B could inhibit cancer cell proliferation, the fusarisetin A and B were added to human breast cancer cell line (MDA-MB-231), mouse fibroblast cell line (3Y1), human liver cancer cell line (Hep3B), human chronic myeloid leukemia cell line (K562), and human promyelocytic leukemia cell line (HL-60) at different concentrations, followed by culture. Then, cell survival rates were investigated. As a result, the fusarisetin A and B of the present invention reduced $IC_{50}$ value (50% inhibition concentration) in MDA-MB-231 cells, 3Y1 cells, Hep3B cells, K562 cells, and HL-60 cells, dose-dependently (see FIGS. 7 and 8). Therefore, it was confirmed that the fusarisetin A and B of the present invention had excellent inhibitory activity on cancer cell proliferation.

To investigate whether or not the fusarisetin A and B could inhibit cancer cell metastasis, the fusarisetin A and B were added to the culture medium of human breast cancer cell line (MDA-MB-231) at different concentrations, followed by culture. Then, metastasis of the cells was measured by using trans-well chamber. As a result, the fusarisetin A and B of the present invention significantly reduced $ED_{100}$ that is the concentration capable of inhibiting metastasis by 100% in MDA-MB-231 cells. Therefore, it was confirmed that the fusarisetin A and B of the present invention had excellent inhibitory activity on cancer cell metastasis. Since the fusarisetin A and B of the present invention could inhibit cell metastasis induced by 10% FBS, it was suggested that the fusarisetin A and B could inhibit factors involved in cancer cell metastasis, for example, integrin, matrix metalloproteinases (MNPs), heparanase, fibroblast growth factor (FGF), etc.

The present invention also provides a fungus strain *Fusarium* sp. FN080326 producing the fusarisetin A or B compound deposited under the Accession No. of KCTC11985BP.

The present invention also provides a method for separating the fusarisetin A or B compound from the *Fusarium* sp. FN080326 strain of the invention.

Particularly, the present invention provides a method for separating the fusarisetin compounds of the invention comprising the following steps:
1) culturing *Fusarium* sp. FN080326 strain; and
2) separating fusarisetin compounds from the culture product of the strain obtained in step 1).

In a preferred embodiment of the present invention, the separation of the fusarisetin compounds was performed as follows:
1) culturing *Fusarium* sp. FN080326 strain;
2) extracting the culture product obtained in step 1) by using ethylacetate; and
3) separating the ethylacetate extract obtained in step 2) by column chromatography.

In the above method, step 1 is to culture *Fusarium* sp. FN080326 strain, in which the strain is preferably the *Fusarium* sp. FN080326 strain deposited under the Accession No. of KCTC11985BP.

The strain culture can be performed in the medium supplemented with nutrition sources for general microorganisms. The nutrition sources can be any conventional ones used for fungi culture. As a carbon source, glucose, starch syrup, dextrin, starch, molasses, animal oil, and vegetable oil can be used. As nitrogen source, wheat bran, soybean meal, wheat, malt, cotton seed meal, fish scrap, corn step liquor, gravy, yeast extract, ammonium sulfate, sodium nitrate, and urea can be used. If necessary, common salt, potassium, magnesium, cobalt, chlorine, phosphate, sulfate, and other inorganic salts accelerating ion production can be added. The culture can be performed by shaking culture or stationary culture in aerobic condition, but not always limited thereto.

The culture temperature which can be adjusted according to the culture condition is preferably 20~37° C., and more preferably 25~30° C., but not always limited thereto.

In the above method, step 2) is to extract the culture product obtained in step 1) by using ethylacetate, in which the fusarisetin A or B compound of the present invention can be found not only in the culture medium of the strain but also in mycelium of the strain. So, it is preferred to add organic solvent such as ethylacetate to the culture medium and mycelium of the strain to extract effective ingredient therefrom, followed by concentrating the ethylacetate extract under the reduced pressure, but not always limited thereto.

In the above method, step 3) is to separate the fusarisetin A or B compound of the present invention, in which flash column chromatography is performed with the ethylacetate extract obtained in step 2) by using the mixed solvent (methanol:water), followed by high performance liquid chromatography for the separation and purification.

The present invention also provides a pharmaceutical composition for the prevention and treatment of cancer comprising the fusarisetin A or B compound of the invention as an active ingredient.

The fusarisetin A or B compound of the present invention has an inhibitory effect on the proliferation and metastasis of cancer cells such as breast cancer cells, liver cancer cells, or myeloid leukemic cells, so that the said fusarisetin A or B compound can be effectively used as an active ingredient for an anticancer agent.

The composition comprising the fusarisetin A or B compound or pharmaceutically acceptable salts thereof of the present invention as an active ingredient can be used in general forms of pharmaceutical formulation.

That is, the fusarisetin A or B compound of the present invention can be prepared for oral or parenteral administration. The composition of the present invention can include one or more pharmaceutically acceptable carriers in addition to the fusarisetin A or B compound, the active ingredient. The pharmaceutically acceptable carrier can be selected or be prepared by mixing more than one ingredients selected from the group consisting of saline, sterilized water, Ringer's solution, buffered saline, dextrose solution, maltodextrose solution, glycerol and ethanol. Other general additives such as anti-oxidative agent, buffer solution, bacteriostatic agent, etc., can be added.

Solid formulations for oral administration are tablets, pills, powders, granules and capsules. These solid formulations are prepared by mixing the active ingredient with one or more suitable excipients such as starch, calcium carbonate, sucrose or lactose, gelatin, etc. Except for the simple excipients, lubricants, for example magnesium stearate, talc, etc, can be used.

Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The pharmaceutical composition of the present invention can be administered parenterally and the parenteral administration includes subcutaneous injection, intravenous injection, and intramuscular injection. To prepare the pharmaceutical composition as a formulation for parenteral administration, the fusarisetin A or B compound is mixed with a stabilizer or a buffering agent to produce a solution or suspension, which is then formulated as ampoules or vials.

The fusarisetin A or B compound of the present invention is preferably included in the pharmaceutical composition of the invention at the concentration of 0.1~50 weight% by the total weight of the composition, but not always limited thereto, and the ratio can be adjusted by considering patient's condition, type and progress of disease, etc.

The effective dosage of the fusarisetin A or B compound of the present invention can be determined according to weight and condition of a patient, severity of a disease, preparation of a drug, administration pathway and time. The effective dosage is preferably 0.01 mg/kg-10 g/kg per day, and more preferably 1 mg/kg-1 g/kg per day. The administration frequency can be once a day or a few times a day. The above dosage cannot limit the scope of the invention in any way.

The present invention also provides a health food for the prevention and improvement of cancer comprising the fusarisetin A or B compound of the invention as an active ingredient.

The fusarisetin A or B compound of the present invention has an inhibitory effect on the proliferation and metastasis of cancer cells such as breast cancer cells, liver cancer cells, or myeloid leukemic cells, so that the said fusarisetin A or B compound can be effectively used as an active ingredient for an anticancer health food.

The food herein is not limited. For example, the fusarisetin A or B compound of the present invention can be added to beverages, gums, vitamin complex, or health additives, and in wide sense, almost every food applicable in the production of health food can be included.

The composition for health beverages of the present invention can additionally include various flavors or natural carbohydrates, etc, like other beverages. The natural carbohydrates above can be one of monosaccharides such as glucose and fructose, disaccharides such as maltose and sucrose, polysaccharides such as dextrin and cyclodextrin, and glucose alcohols such as xilytole, sorbitol and erythritol. Besides, natural sweetening agents such as thaumatin and stevia extract, and synthetic sweetening agents such as saccharin and aspartame can be included as a sweetening agent. The content of the natural carbohydrate is preferably 0.01-0.04 g and more preferably 0.02-0.03 g in 100 ml of the composition.

In addition to the ingredients mentioned above, the composition of the present invention can include in a variety of nutrients, vitamins, minerals, flavors, coloring agents, pectic acid and its salts, alginic acid and its salts, organic acid, protective colloidal viscosifiers, pH regulators, stabilizers, antiseptics, glycerin, alcohols, carbonators which used to be added to soda, etc. The composition of the present invention can also include natural fruit juice, fruit beverages and/or fruit flesh addable to vegetable beverages. All the mentioned ingredients can be added singly or together. The mixing ratio of those ingredients does not matter in fact, but in general, each can be added by 0.01-0.1 weight part per 100 weight part of the composition of the present invention.

The present invention also provides a method for the treatment of cancer containing the step of administering a pharmaceutically effective dose of the said compound or pharmaceutically acceptable salts thereof to a subject having cancer.

The present invention also provides a method for the prevention of cancer containing the step of administering a pharmaceutically effective dose of the said compound or pharmaceutically acceptable salts thereof to a subject.

The fusarisetin A or B compound of the present invention has an inhibitory effect on the proliferation and metastasis of cancer cells such as breast cancer cells, liver cancer cells, or myeloid leukemic cells, so that the said fusarisetin A or B compound can be effectively used for the prevention or treatment of cancer.

The present invention also provides the said compound or pharmaceutically acceptable salts thereof for the use as a pharmaceutical composition for the prevention and treatment of cancer.

The present invention also provides the said compound or pharmaceutically acceptable salts thereof for the use as a health food for the prevention and improvement of cancer.

The fusarisetin A or B compound of the present invention has an inhibitory effect on the proliferation and metastasis of cancer cells such as breast cancer cells, liver cancer cells, or myeloid leukemic cells, so that the said fusarisetin A or B compound can be effectively used as an active ingredient for an anticancer agent.

The food herein is not limited. For example, the fusarisetin A or B compound of the present invention can be added to beverages, gums, vitamin complex, or health additives, and in wide sense, almost every food applicable in the production of health food can be included.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

EXAMPLE 1

Isolation of *Fusarium* sp. FN080326 Strain

The strain was isolated from a soil sample obtained in the area near Daejeon, Korea in March, 2008. The soil sample was put in a sterilized plastic bag right after picking up, which was stored in a freezer until use. The soil sample was 10-fold diluted in sterilized distilled water. 1 ml of the diluted solution was smeared on potato dextrose agar medium, followed by culture at 28° C. for 5 days. Colonies shown on the agar medium were collected and purified.

EXAMPLE 2

Identification and Naming of the Strain

Figure 6:
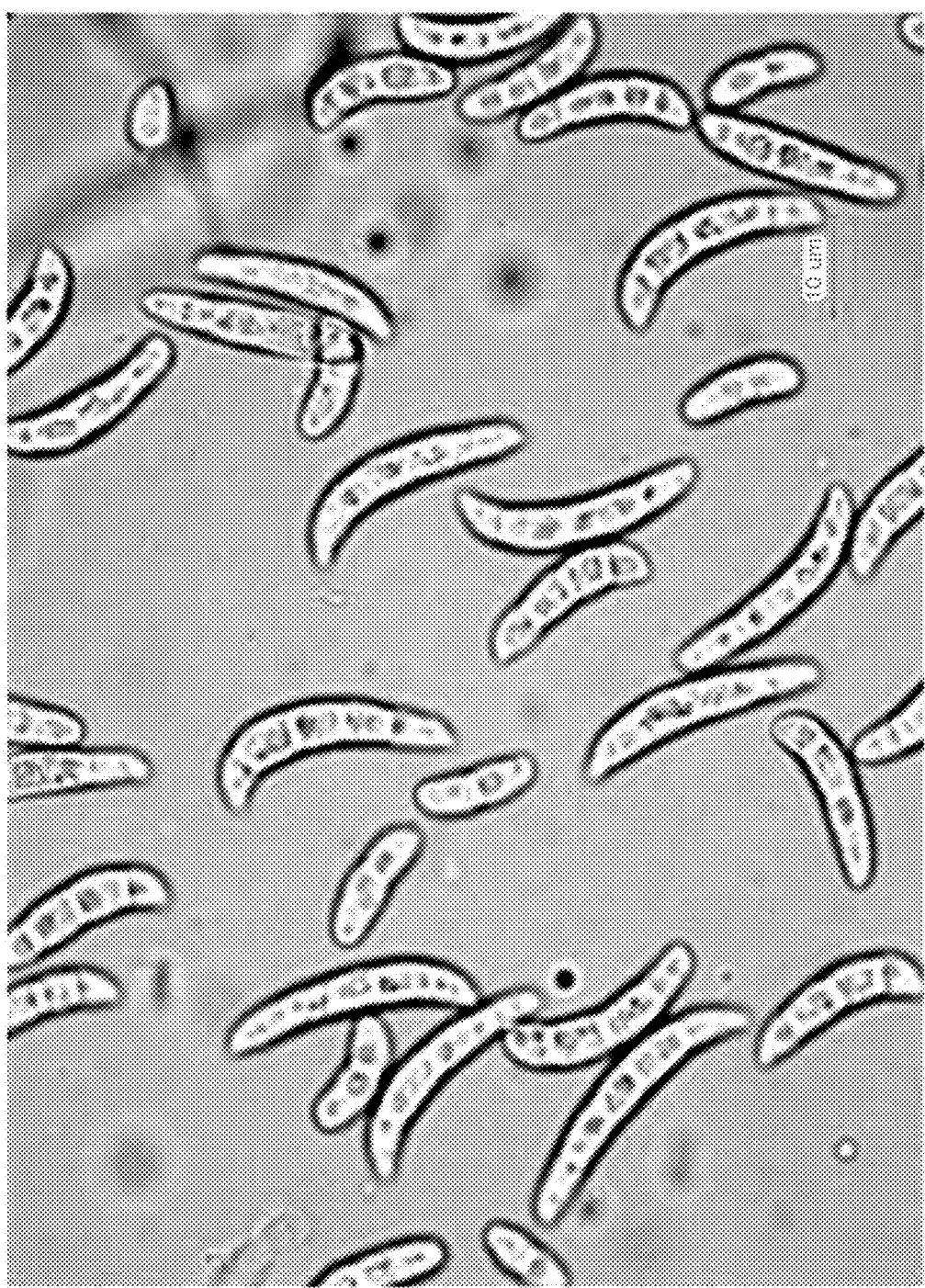
FIG. 6 is a photomicrograph showing the *Fusarium* sp. FN080326 isolated in this invention.

Spores of the strain were observed under microscope (FIG. 6) and rNRA sequence analysis was performed. As a result, the ITS, 26S, and 18S rRNA sequences of the strain were as follows:

```
ITS (506 bp)
                                                  (SEQ. ID. NO: 1)
AGGGATCATTACCGAGTTTACAACTCCCAAACCCCTGTGAACATACCTATACGTTGC

CTCGGCGGATCAGCCCGCGCCCCGTAAAACGGGACGGCCCGCCCGAGGACCCTAAACTCTGT

TTTTAGTGGAACTTCTGAGTAAAACAAACAAATAAATCAAAACTTTCAACAACGGATCTCTT

GGTTCTGGCATCGATGAAGAACGCAGCAAAATGCGATAAGTAATGTGAATTGCAGAATTCAG

TGAATCATCGAATCTTTGAACGCACATTGCGCCCGCCAGTATTCTGGCGGGCATGCCTGTTC

GAGCGTCATTTCAACCCTCAAGCTCAGCTTGGTGTTGGGACTCGCGGTAACCCGCGTTCCCC

AAATCGATTGGCGGTCACGTCGAGCTTCCATAGCGTAGTAATAATACACCTCGTTACTGGTA

ATCGTCGCGGCCACGCCGTAAAACCCCAACTTCTGAATGTTGACCTCGGATCAGGTAGGAAT

ACCCGCTGAACTTAA 26S (563 bp)
                                                  (SEQ. ID. NO: 2)
AAACCAACAGGGATTGCCCTAGTAACGGCGAGTGAAGCGGCAACAGCTCAAATTTGA

AATCTGGCTCTCGGGCCCGAGTTGTAATTTGTAGAGGATGCTTTTGATGCGGTGCCTTCCGA

GTTCCCTGGAACGGGACGCCATAGAGGGTGA

GAGCCCCGTCTGGTTGGATACCAAATCTCTGTAAAGCTCCTTCGACGAGTCGAGTAG

TTTGGGAATGCTGCTCTAAATGGGAGGTATATGTCTTCTAAAGCTAAATACTGGCCAGAGAC

CGATAGCGCACAAGTAGAGTGATCGAAAGATGAAAAGCACTTTGAAAAGAGAGTTAAAAAGT

ACGTGAAATTGTTGAAAGGGAAGCGTTTATGACCAGACTTGGGCTTGGATAATCATCTGGGG

TTCTCCCCAGTGCACTTTTCCAGTCCAGGCCAGCATCAGTTTTCGCCGGGGATAAAGGCTT

CGGGAATGTGGCTCCCTCCGGGGAGTGTTATAGCCCGTTGCGTAATACCCTGGCGGGGACTG

AGGTTCGCGCATCTGCAAGGATGCTGGCGTAATGGTCATCAACGAC
```

-continued 18S (1675 bp)
(SEQ. ID. NO: 3)
CATTATACCGCGAAACTGCGAATGGCTCATTATATAAGTTATCGTTTATTTGATAGT

ACCTTACTACTTGGATAACCGTGGTAATTCTAGAGCTAATACATGCTAAAAATCCCGACTTC

GGAAGGGATGTATTTATTAGATTAAAAACCAATGCCCTTCGGGGCTCACTGGTGATTCATGA

TAACTCCTCGAATCGCATGGCCTTGTGCCGGCGATGGTTCATTCAAATTTCTTCCCTATCAA

CTTTCGATGTTTGGGTATTGGCCAAACATGGTTGCAACGGGTAACGGAGGGTTAGGGCTCGA

CCCCGGAGAAGGAGCCTGAGAAACGGCTACTACATCCAAGGAAGGCAGCAGGCGCGCAAATT

ACCCAATCCCGACACGGGGAGGTAGTGACAATAAATACTGATACAGGGCTCTTTTGGGTCTT

GTAATTGGAATGAGTACAATTTAAATCCCTTAACGAGGAACAATTGGAGGGCAAGTCTGGTG

CCAGCAGCCGCGGTAATTCCAGCTCCAATAGCGTATATTAAAGTTGTTGTGGTTAAAAAGCT

CGTAGTTGAACCTTGGGCCTGGCCGTCCGGTCCGCCTCACCGCGTGTACTGGCTCGGCCGGG

CCTTTCCCTCTGTGGAACCCCATGCCCTTCACTGGGCGTGGCGGGGAAACAGGACTTTTACT

GTGAAAAATTAGAGTGCTCCAGGCAGGCCTATGCTCGAATACATTAGCATGGAATAATAGA

ATAGGACGTGTGGTTCTATTTTGTTGGTTTCTAGGACCGCCGTAATGATTAATAGGGACAGT

CGGGGGCATCAGTATTCAATTGTCAGAGGTGAAATTCTTGGATTTATTGAAGACTAACTACT

GCGAAAGCATTTGCCAAGGATGTTTTCATTAATCAGGAACGAAAGTTAGGGGATCGAAGACG

ATCAGATACCGTCGTAGTCTTAACCATAAACTATGCCGACTAGGGATCGGACGGTGTTATTT

TTTGACCCGTTCGGCACCTTACGAGAAATCAAAGTGCTTGGGCTCCAGGGGAGTATGGTCG

CAAGGCTGAAACTTAAAGAAATTGACGGAAGGGCACCACCAGGGGTGGAGCCTGCGGCTTAA

TTTGACTCAACACGGGGAAACTCACCAGGTCCAGACACAATGAGGATTGACAGATTGAGAGC

TCTTTCTTGATTTTGTGGGTGGTGGTGCATGGCCGTTCTTAGTTGGTGGAGTGATTTGTCTG

CTTAATTGCGATAACGAACGAGACCTTAACCTGCTAAATAGCCCGTATTGCTTTGGCAGTAC

GCTGGCTTCTTAGAGGGACTATCGGCTCAAGCCGATGGAAGTTTGAGGCAATAACAGGTCTG

TGATGCCCTTAGATGTTCTGGGCCGCACGCGCGCTACACTGACGGAGCCAGCGAGTACTTCC

TTGTCCGAAAGGTCCGGGTAATCTTGTTAAACTCCGTCGTGCTGGGGATAGAGCATTGCAAT

TATTGCTCTTCAACGAGGAATCCCTAGTAAGCGCAAGTCATCAGCTTGCGTTGATTACGTCC

CTGCCCTTTGTACACACCGCCCGTCGCTACTACCGATTGAATGGCTCAGTGAGGCGTCCGGA

CTGGCCCAGAGAGGTGGGCAACTACCACTCAGGGCCGGAAAGCTCTCCAAACTCGGTCATTA

GAGAAG

GenBank search was carried out with the obtained sequences. As a result, the strain demonstrated 99% homology with *Fusarium oxysporum* (DQ916150) and 99% homology with *Fusarium incarnatum* (EU111657). Therefore, the present inventors identified the strain as *Fusarium* sp. and then named it *Fusarium* sp. FN080362, which was deposited at Korean Collection for Type Culture (KCTC), Korea Research Institute of Bioscience and Biotechnology (KRIBB) on Jul. 18, 2011 (Accession No: KCTC11985BP).

EXAMPLE 3

Culture of *Fusarium* sp. FN080326 Strain

To culture the fungus strain, a medium supplemented with the nutritions generally used for microorganism culture was prepared. Potato dextrose medium was used as co-medium and production medium for the fungus strain.

Two 500 ml Erlenmeyer flasks containing 150 ml of the medium were sterilized at 121° C. for 20 minutes. The *Fusarium* sp. FN080326 was inoculated in the sterilized flask from the stored plate using platinum loop, followed by shaking-culture for 3 days, leading to seed culture. For main culture, production medium was loaded in two 14 L fermentors (8 L/fermentor), followed by sterilization. Each fermentor was inoculated with 150 ml of the seed culture medium, followed by culture at 28° C., 165 rpm with 10 L/min of airing for 6 days.

EXAMPLE 4

Separation and Purification of Compounds from *Fusarium* sp. FN080326 Strain

The *Fusarium* sp. FN080326 culture solution (16 L) prepared in <Example 3> was extracted with the equal amount of ethylacetate three times. The obtained extract was concentrated by using a vacuum dryer according to the method of vacuum evaporation. The concentrate was absorbed on ODS RP-18, followed by ODS RP-18 flash column chromatography. At this time, the mixed solvent comprising methanol and water (1:9~10:0, v/v) was used. Elution was performed step-wise with increasing the concentration of methanol. The active fraction containing the compounds 1 and 2 was eluted from 80% methanol. The active fraction was concentrated under the reduced pressure. Then, the fraction containing the compounds 1 and 2 proceeded to high performance liquid chromatography (column: RS tech Optima Pak C18, length 250 mm, diameter 10 mm; solvent: 48% acetonitrile; elution rate: 3 ml/min). As a result, the compound 1 (retention time: 42 min) and compound 2 (retention time 45 min) detected at 203 nm and 254nm of UV absorption peak were separated respectively (FIG. 1).

EXAMPLE 5

Structural Analysis of the Compound Separated from the *Fusarium* sp. FN080326 Strain Molecular weights and molecular formulas of the compound and compound 2 separated from the culture solution of *Fusarium* sp. FN080326 were determined by using ESI (Electrospray Ionization mass spectrometer). Nuclear magnetic resonance (NMR) was also performed to give $^1$H, $^{13}$C NMR, COSY (Correlation Spectroscopy), HMQC (1H-Detected heteronuclear Multiple-Quantum Coherence), HMBC (Heteronuclear Multiple-Bond Coherence), DEPT (Distortionless Enhancement by Polarization), and NOESY (Nuclear Overhauser effect spectroscopy) spectrums, by which, molecular structures of the compounds 1 and 2 were identified (FIGS. 2, 3, 4, and 5).

As a result, the compound 1 and compound 2 were identified as the compounds with novel structure in which 6-6-5-5-5 ring chains were connected one another as shown in FIGS. 2-5. Thus, the compound 1 and compound 2 were named as fusarisetin A and fusarisetin B (compounds 1 and 2).

HRESIMS and NMR were performed with the fusarisetin A and fusarisetin B. As a result, it was confirmed that their molecular weights were 389 each and molecular formula was $C_{22}H_{31}NO_5$. From the results of $^1$H NMR and NOESY, it was also confirmed that the compounds 1 and 2 were the isomers having the same molecular weight and molecular formula with different three-dimensional coordinations of $C_5$.

[Formula 1]

fusarisetin A (compound 1): white powder; $[\alpha]_D$ +84.6 (c 0.2, MeOH); UV(MeOH) $\lambda_{max}$ (log ε) 208 (2.34), 282(2.36); IR (neat) $\upsilon_{max}$ 3325, 2925, 1734, 1666, 1451, 1402, 1376, 1172, 1075 cm$^{-1}$; $^1$H and $^{13}$C NMR data are shown in Table 1; HRESIMS m/z 412.2085 [M+Na]$^+$ (calcd for $C_{22}H_{31}NO_5Na$, 412.2100).

[Formula 2]

fusarisetin B (compound 2): white powder; $[\alpha]_D$ +84.9 (c 0.2, MeOH); UV(MeOH) $\lambda_{max}$ (log ε) 208 (2.34), 281(3.18); IR (neat) $\upsilon_{max}$ 3325, 2925, 1734, 1666, 1451, 1402, 1376, 1172, 1075 cm$^{-1}$; $^1$H and $^{13}$C NMR data are shown in Table 1; HRESIMS m/z 412.2094 [M+Na]$^+$ (calcd for $C_{22}H_{31}NO_5Na$, 412.2100).

TABLE 1

$^1$H and $^{13}$C NMR data of compounds 1 and 2 (Acetone-d$_6$)

| | A | | B | |
|---|---|---|---|---|
| position | $\delta_C{}^a$ | $\delta_H$, mult. (J in Hz)$^b$ | $\delta_C{}^a$ | $\delta_H$, mult. (J in Hz)$^b$ |
| 1 | 75.6 | | 75.6 | |
| 2 | 170.0 | | 170.5 | |
| 3 | 70.2 | 3.55 dd (6.0, 3.0) | 68.5 | 3.50 dd (5.2, 4.8) |
| 4 | 109.5 | | 110.0 | |
| 5 | 78.7 | 4.33 dd (6.4) | 83.5 | 4.55 dd (5.2) |
| 6 | 55.8 | 2.82 dd (10.8, 5.2) | 59.3 | 2.56 dd (8.0, 7.6) |
| 7 | 44.1 | 2.64 dd (10.8, 4.8) | 51.1 | 2.42 dd (8.4, 8.0) |
| 8 | 127.9 | 5.80 m | 126.4 | 5.84 m |
| 9 | 133.0 | 5.54 br d (10.0) | 132.5 | 5.52 br d (10.0) |
| 10 | 37.4 | 1.87 m | 37.3 | 1.85 m |
| 11 | 42.8 | 1.85 m 0.81 dd (12.8, 12.0) | 42.8 | 1.84 m 0.85 dd (10.4, 9.6) |
| 12 | 33.7 | 1.48 m | 33.7 | 1.48 dd (8.0) |
| 13 | 36.1 | 1.73 br d (13.2) 0.91 ddd | 36.0 | 1.72 m 0.91 ddd |
| 14 | 26.1 | 1.54 m 1.09 dddd | 26.1 | 1.66 1.05 dddd |
| 15 | 38.4 | 1.52 m | 37.7 | 1. 68 m |
| 16 | 54.7 | | 55.6 | |
| 17 | 213.0 | | 212.6 | |
| 18 | 60.6 | 3.92 dd (11.6, 3.6) 3.80 dd (11.6, 6.0) | 60.9 | 3.97 dd (9.2) 3.89 dd (9.2, 8.8) |
| 19 | 29.0 | 2.88 s | 29.6 | 2.89 s |
| 20 | 17.7 | 1.41 d (6.8) | 22.8 | 1.18 d (5.2) |
| 21 | 22.8 | 0.90 d (6.4) | 22.7 | 0.90 d (4.8) |
| 22 | 14.3 | 0.95 s | 14.6 | 0.92 s |

$^a$measured at 100 MHz.
$^b$measured at 400 MHz.

EXPERIMENTAL EXAMPLE 1

Measurement of Inhibitory Activity of the Compounds of the Present Invention on Cancer Cell Proliferation Following experiment was performed to investigate the inhibitory activity of the compounds 1 and 2 of the present invention on the proliferation of cancer cells.

Particularly, human breast cancer cell line (MDA-MB-231, 5.0×10$^3$ cells per well), mouse fibroblast cell line (3Y1, 5.0× 10$^3$ cells per well), and human liver cancer cell line (Hep3B, 5.0×10$^3$ cells per well) were cultured respectively in DMEM (Dulbecco's modification of Eagles medium, supplemented with 10% FBS). And human chronic myeloid leukemia cell line (K562, 3.0×10$^4$ cells per well) and human promyelocytic leukemia cell line (HL-60, 1.0×10$^5$ cells per well) were cultured respectively in RPMI 1640 (Roswell Park Memorial Institute 1640 medium, supplemented with 10% FBS). Each cell line cultured above was treated with different concentrations of the compound 1 and compound 2 (100 μg/ml, 30 μg/ml, 10 μg/ml, 3 μg/ml, and 1 μg/ml), followed by culture in a 5% $CO_2$ incubator for 48 hours at 37° C. WST-8 reagent (2-(2-methoxy-4-nitrophenyl)-3-(4-nitrophenyl)-5-(2,4-disulfophenyl)-2H-tetrazolium, monosodium salt) producing high sensitive water soluble formazan was added thereto, followed by further culture for 24 hours. OD$_{450}$ was measured to calculate cell survival rate.

Figure 7:
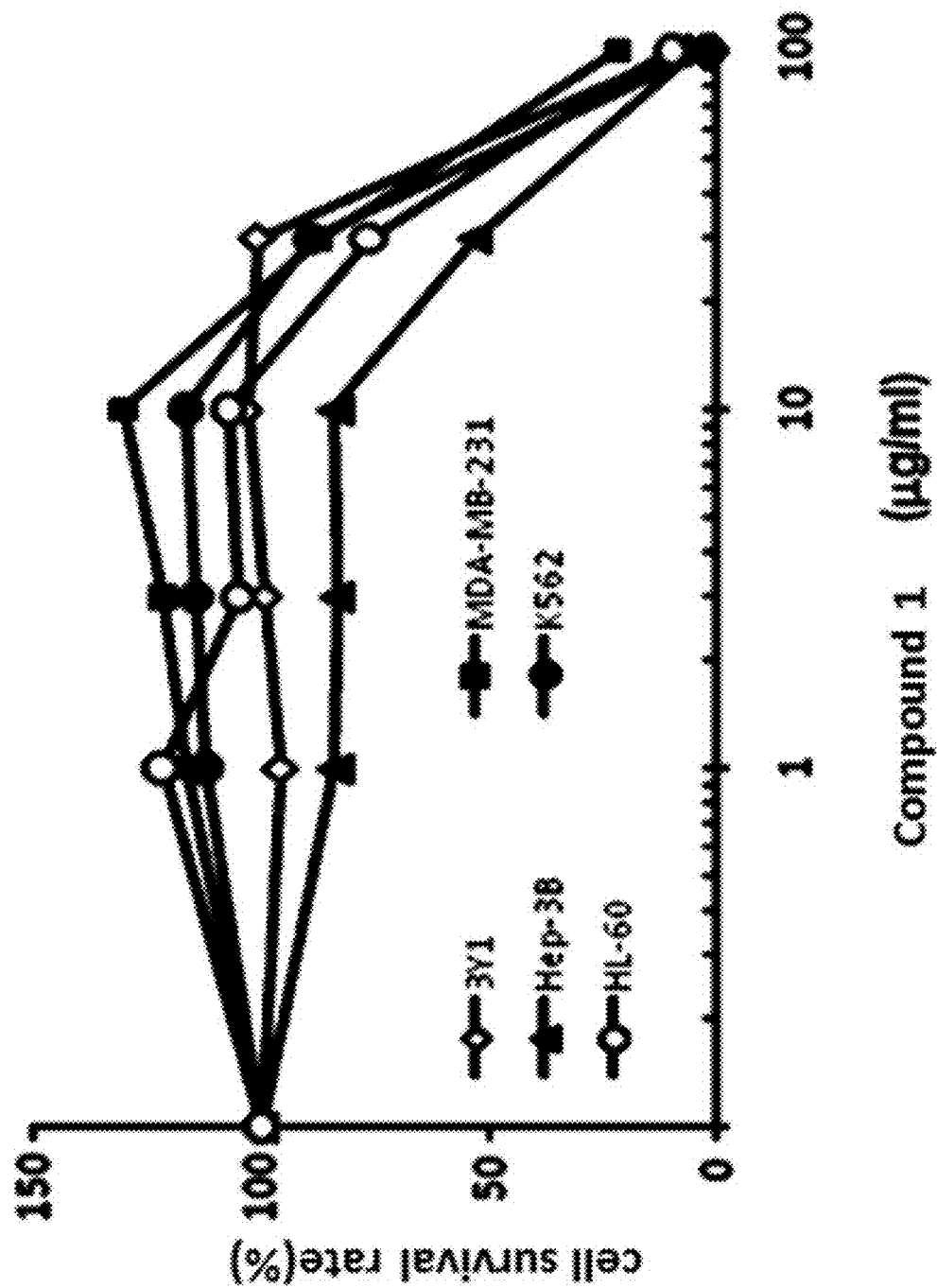
FIG. 7 is a diagram illustrating the inhibitory effect of the compound 1 (Fusarisetin A) separated in this invention on the proliferation of cancer cells.
Figure 8:
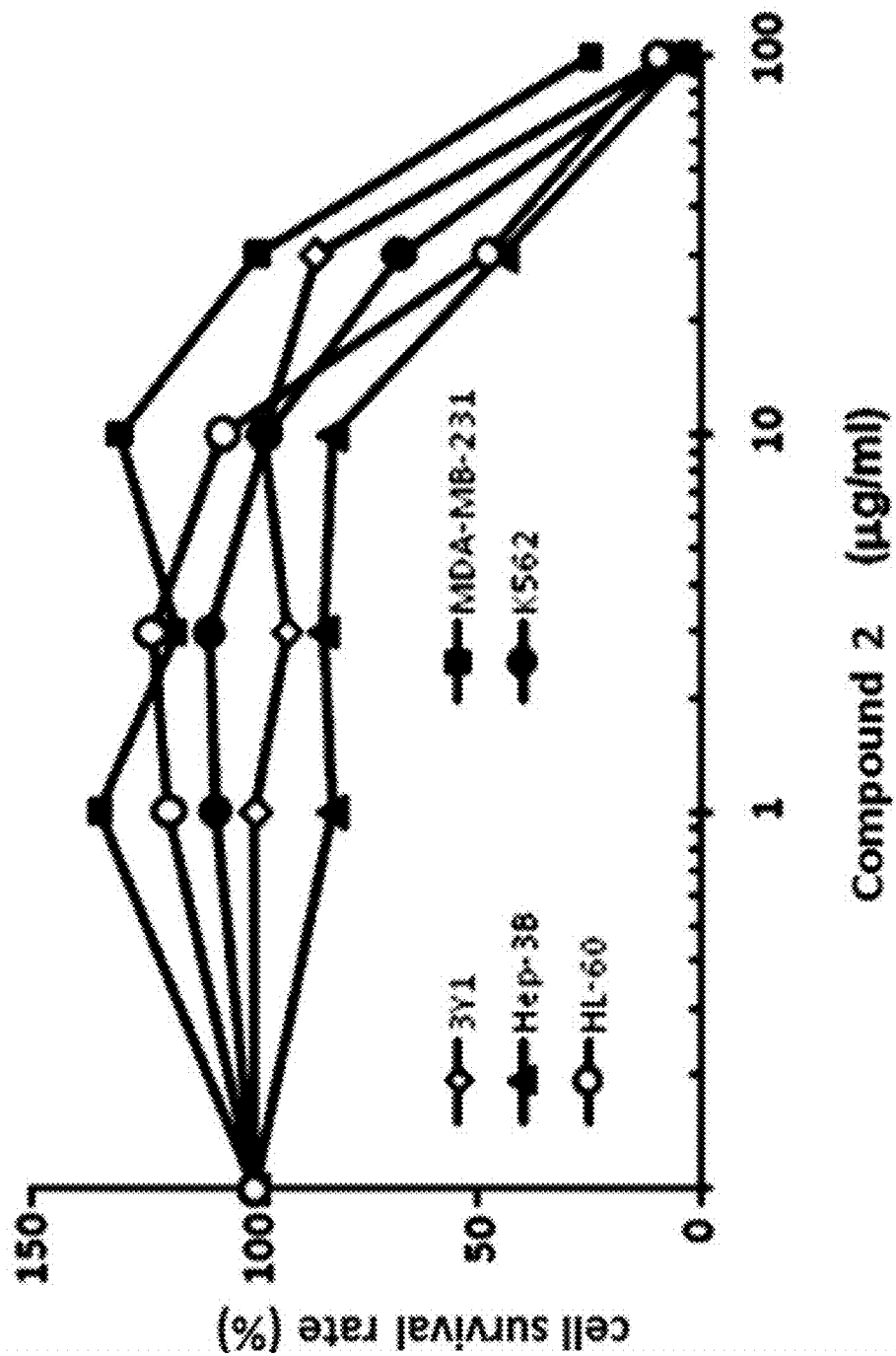
FIG. 8 is a diagram illustrating the inhibitory effect of the compound 2 (Fusarisetin B) separated in this invention on cancer cell proliferation.

As a result, as shown in FIG. 7 and FIG. 8, $IC_{50}$ of the compound 1 to each MDA-MB-231 cell line, 3Y1 cell line, Hep3B cell line, K562 cell line, and HL-60 cell line was respectively 69.5 μg/ml, 67.5 μg/ml, 34.7 μg/ml, 61.3 μg/ml, and 57.7 μg/ml. In the meantime, $IC_{50}$ of the compound 2 to each cell line was respectively 76.5 μg/ml, 62.2 μg/ml, 27.2 μg/ml, 49.3 μg/ml, and 29.4 μg/ml (FIG. 7 and FIG. 8). Therefore, it was confirmed that the compounds of the present invention had an inhibitory activity on the proliferation of cancer cells.

EXPERIMENTAL EXAMPLE 2

Measurement of Inhibitory Activity of the Fusarisetin Compounds of the Present Invention on Cancer Cell Metastasis Trans-well chamber (BioCoat™ Matrigel™ Invasion Chamber, pore size 8 μm, BD Biosciences, Bedford, Mass.) was used for the investigation of inhibitory activity of the compounds of the present invention on cancer cell metastasis. Particularly, human breast cancer cells (MDA-MB-231 cells) were distributed on the upper part of the chamber at the density of $1.0 \times 10^5$ cells per well. DMEM (Dulbecco's modification of Eagles medium, serum-free) was used for the culture. 30 minutes later, the compounds 1 and 2 were added to the upper part of the chamber at different concentrations of 30 μg/ml, 10 μg/ml, and 3 μg/ml, respectively. 30 minutes later, 10% FBS was added to the bottom of the chamber, followed by culture in a 5% $CO_2$ incubator at 37° C. for 24 hours. 24 hours later, the cells migrated through porous membrane which had been induced by 10% FBS in the bottom of the chamber were fixed with 100% MeOH, followed by staining with Wright stain. Upon completion of the staining, the migrated cells were counted under microscope.

Figure 9:
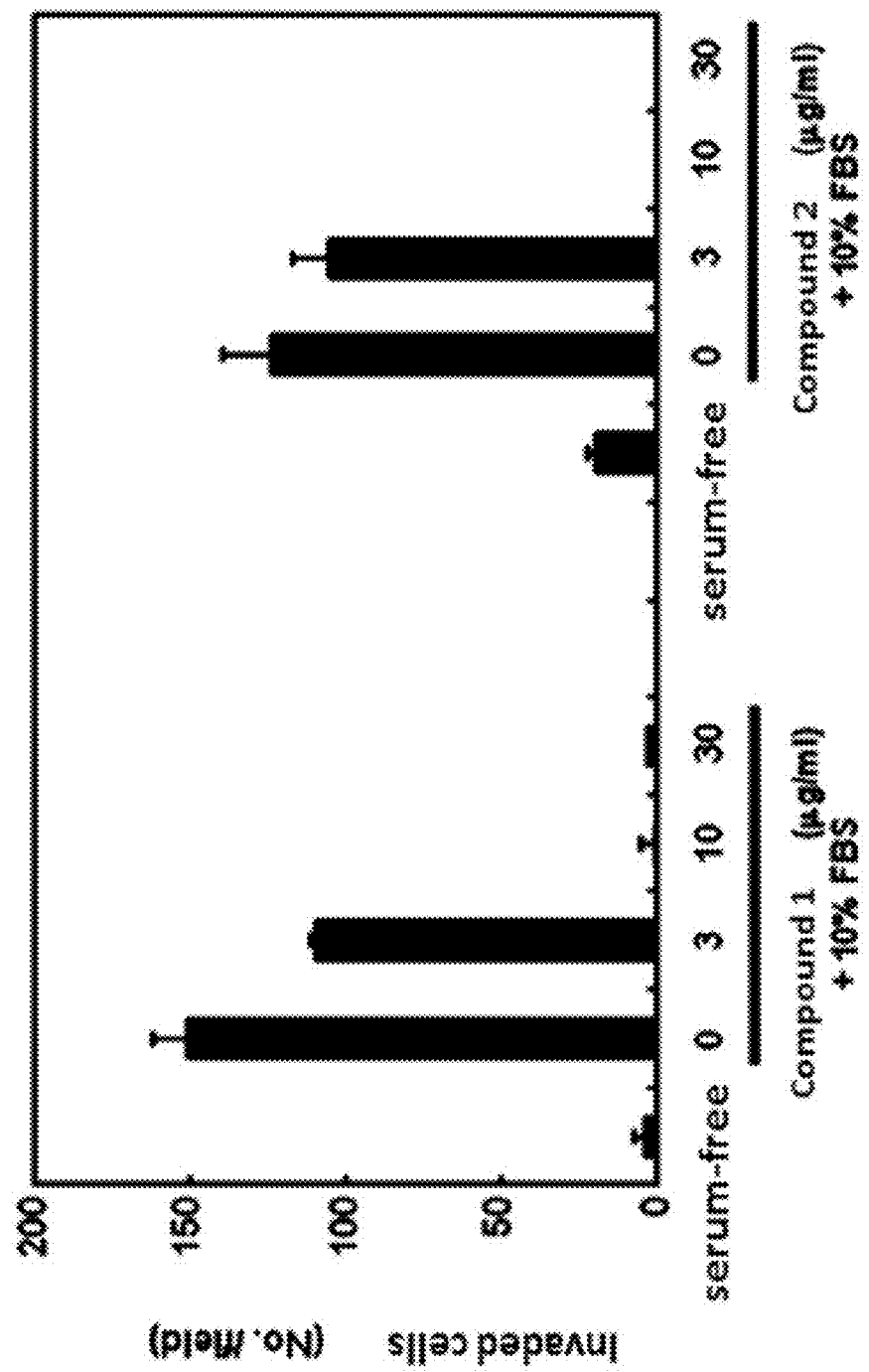
FIG. 9 is a diagram illustrating the inhibitory effect of the compound 1 and compound 2 (fusarisetin A and B), separated in this invention on cancer cell metastasis.

As a result, as shown in FIG. 9, $ED_{100}$ indicating the concentration capable of inhibiting metastasis of human breast cancer cell line by 100% was confirmed to be 10 μg/ml (FIG. 9). Since the compounds 1 and 2 of the present invention could inhibit cell metastasis induced by 10% FBS, it was suggested that the compounds 1 and 2 could inhibit factors involved in cancer cell metastasis, for example, integrin, matrix metalloproteinases (MNPs), heparanase, fibroblast growth factor (FGF), etc. Therefore, it was confirmed that the compounds 1 and 2 of the present invention had excellent inhibitory activity on cancer cell metastasis.

MANUFACTURING EXAMPLE 1

Preparation of Powders

| | |
|---|---|
| Fusarisetin A | 20 mg |
| Lactose | 100 mg |
| Talc | 10 mg |

Powders were prepared by mixing all the above components, which were filled in airtight packs according to the conventional method for preparing powders.

MANUFACTURING EXAMPLE 2

Preparation of Tablets

| | |
|---|---|
| Fusarisetin A | 10 mg |
| Corn starch | 100 mg |
| Lactose | 100 mg |
| Magnesium stearate | 2 mg |

Tablets were prepared by mixing all the above components by the conventional method for preparing tablets.

MANUFACTURING EXAMPLE 3

Preparation of Capsules

| | |
|---|---|
| Fusarisetin A | 10 mg |
| Crystalline cellulose | 3 mg |
| Lactose | 14.8 mg |
| Magnesium stearate | 0.2 mg |

Capsules were prepared by mixing all the above components, which were filled in gelatin capsules according to the conventional method for preparing capsules.

MANUFACTURING EXAMPLE 4

Preparation of Injectable Solutions

| | |
|---|---|
| Fusarisetin B | 10 mg |
| Mannitol | 180 mg |
| Injectable sterilized distilled water | 2974 mg |
| $Na_2HPO_4, 12H_2O$ | 26 mg |

Injectable solutions were prepared by mixing all the above components, which were filled in ampoules (2 ml/ampoule) according to the conventional method for preparing injectable solutions.

MANUFACTURING EXAMPLE 5

Preparation of Liquid Formulations

| | |
|---|---|
| Fusarisetin B | 20 mg |
| Isomerized sugar | 10 g |
| Mannitol | 5 g |
| Purified water | proper amount |

All the above components were dissolved in purified water. After adding lemon flavor, total volume was adjusted to be 100 μl by adding purified water. Liquid formulations were prepared by putting the mixture into brown bottles and sterilizing thereof by the conventional method for preparing liquid formulations.

MANUFACTURING EXAMPLE 6

Preparation of Health Food

| | |
|---|---|
| Fusarisetin A | 1000 mg |
| Vitamin complex | proper amount |
| Vitamin A acetate | 70 μg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 μg |
| Vitamin C | 10 mg |
| Biotin | 10 μg |
| Nicotinic acid amide | 1.7 mg |
| Folic acid | 50 μg |
| Calcium pantothenate | 0.5 mg |
| Minerals | proper amount |
| Ferrous sulfate | 1.75 mg |
| Zinc oxide | 0.82 mg |
| Magnesium carbonate | 25.3 mg |
| Potassium phosphate monobasic | 15 mg |
| Potassium phosphate dibasic | 55 mg |
| Potassium citrate | 90 mg |
| Calcium carbonate | 100 mg |
| Magnesium chloride | 24.8 mg |

Vitamins and minerals were mixed according to the preferable composition rate for health food. However, the composition rate can be adjusted. The constituents were mixed according to the conventional method for preparing health food and then the composition for health food was prepared according to the conventional method.

MANUFACTURING EXAMPLE 7

Preparation of Health Beverages

| | |
|---|---|
| Fusarisetin B | 1000 mg |
| Citric acid | 1000 mg |
| Oligosaccharide | 100 g |
| Maesil (*Prunus mume*) Extract | 2 g |
| Taurine | 1 g |
| Purified water | up to 900 ml |

The above constituents were mixed according to the conventional method for preparing health beverages. The mixture was heated at 85° C. for 1 hour with stirring and then filtered. The filtrate was loaded in 2 liter sterilized containers, which were sealed and sterilized again, stored in a refrigerator until they would be used for the preparation of a composition for health beverages.

The constituents appropriate for favorite beverages were mixed according to the preferred mixing ratio but the composition ratio can be adjusted according to regional and national preferences, etc.

INDUSTRIAL APPLICABILITY

As explained hereinbefore, the novel fusarisetin compounds of the present invention can be mass-produced by using *Fusarium* sp. FN080326 strain according to the method of the invention, and the novel fusarisetin compounds of the invention can be effectively used for the development of an anticancer agent or an anticancer health food.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A compound of formula 3 or pharmaceutically acceptable salts thereof:

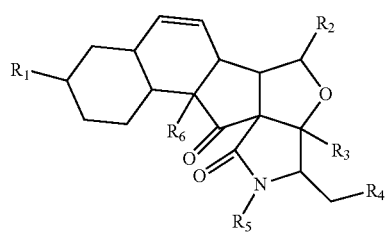

[Formula 3]

wherein, $R_{1-6}$ are independently H, methyl, ethyl, propyl, isopropyl, butyl, isobutyl, acetyl, benzyl, halogen atom, OH, or carboxyl group, and contain isomers at all asymmetric carbons.

2. The compound or the pharmaceutically acceptable salts thereof according to claim 1, wherein the compound is the fusarisetin A compound of formula 1:

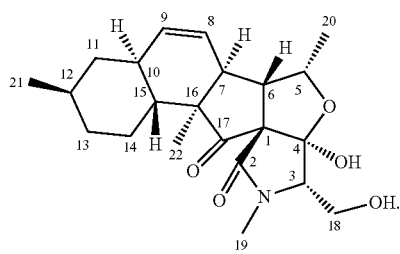

[Formula 1]

3. The compound or the pharmaceutically acceptable salts thereof according to claim 1, wherein the compound is the fusarisetin B compound of formula 2:

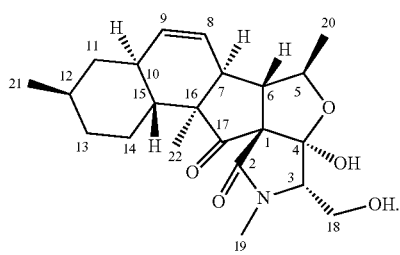

[Formula 2]

4. The compound or the pharmaceutically acceptable salts thereof according to claim 1, wherein the fusarisetin compound is separated from the fungus *Fusarium* sp. FN080326.

5. A composition for treatment of cancer comprising the compound or the pharmaceutically acceptable salts thereof of claim 1, wherein the cancer is breast cancer, liver cancer, or myeloid leukemia.

6. A method for producing the compound of claim 1 comprising the following steps:
   1) culturing *Fusarium* sp. FN080326 strain; and
   2) separating fusarisetin compounds from the culture product of the strain obtained in step 1).

7. A method for treating cancer comprising:
   administering a pharmaceutically effective dose of the compound or the pharmaceutically acceptable salts thereof of claim 1 to a subject having a cancer, wherein the cancer is breast cancer, liver cancer, or myeloid leukemia.

* * * * *